(12) United States Patent
Penney

(10) Patent No.: US 8,992,995 B2
(45) Date of Patent: Mar. 31, 2015

(54) SKIN CARE OINTMENT

(75) Inventor: Donna Penney, Southold, NY (US)

(73) Assignee: Bay Song Art, Inc., Southold, NY (US)

( * ) Notice: Subject to any disclaimer, the term of this patent is extended or adjusted under 35 U.S.C. 154(b) by 290 days.

(21) Appl. No.: 12/848,544

(22) Filed: Aug. 2, 2010

(65) Prior Publication Data

US 2012/0027868 A1  Feb. 2, 2012

(51) Int. Cl.
*A61K 35/64* (2006.01)
*A61K 8/27* (2006.01)
*A61K 8/92* (2006.01)
*A61K 8/97* (2006.01)
*A61Q 19/00* (2006.01)

(52) U.S. Cl.
CPC .............. *A61K 35/644* (2013.01); *A61K 8/27* (2013.01); *A61K 8/925* (2013.01); *A61K 8/927* (2013.01); *A61K 8/97* (2013.01); *A61Q 19/00* (2013.01)
USPC ........................................................ 424/537

(58) Field of Classification Search
CPC ......... A61K 35/644; A61K 8/27; A61K 8/97; A61K 8/925; A61Q 19/00
See application file for complete search history.

(56) References Cited

U.S. PATENT DOCUMENTS

| 5,242,952 | A  | * | 9/1993 | Tritsarolis | ..................... 514/783 |
| 5,997,889 | A  | * | 12/1999 | Durr et al. | ..................... 424/401 |
| 7,029,711 | B2 | * | 4/2006 | Farrell | .......................... 424/725 |
| 2002/0082279 | A1 | * | 6/2002 | Schultz | .......................... 514/330 |
| 2008/0286299 | A1 | * | 11/2008 | Battaglia | .................. 424/195.18 |

OTHER PUBLICATIONS

Lansdown et al., Zinc in wound healing: Theoretical, experimental and clinical aspects, 2007, Wound Repair and Regeneration 15(1): 2-16.*
Zincuta website "Zincuta", www.zincuta.com, accessed on May 28, 2014, pp. 1-15.*
Duluth Trading website "Zincuta", http://www.duluthtrading.com/store/product/zincuta-36556.aspx accessed [May 30, 2014 10:39:54 AM], 2 pages.*

* cited by examiner

*Primary Examiner* — Robert Yamasaki
(74) *Attorney, Agent, or Firm* — Tarter Krinsky & Drogin LLP

(57) ABSTRACT

An improved topical cosmetic skin formulation is provided. The inventive formulation includes leaf lard as a base, zinc oxide and beeswax. In addition, slippery elm bark may be added to the formulation. Further, benzoin styrax may be added to the inventive formulation.

10 Claims, No Drawings

SKIN CARE OINTMENT

BACKGROUND OF THE INVENTION

The present invention refers to a topical ointment formulation with all natural ingredients to be applied to the skin. The ointment penetrates, softens, soothes, protects and heals all afflictions of the surface of the skin. This happens due to the synergistic combination of chemical constituents in the formulation. The formulation can be used for chafes; fire, sun and wind burns; raw sores, insect bites and stings, eczema, psoriasis, abrasions, chapped/cracked lips, conditions on the hands and feet, poison ivy, hemorrhoids and as a sunblock.

The formulation of the invention is advantageous over many topical competitive products as it contains no synthesized ingredients. In contrast to other cosmetic formulations, it contains neither an animal nor a vegetable fat. Further, with the present inventive formulation, no water is added in the process of manufacture.

SUMMARY OF THE INVENTION

Generally speaking, in accordance with the invention, an improved topical cosmetic skin formulation is provided. The inventive formulation includes leaf lard as a base, zinc oxide of a preferred amount of between about 10 and 25 weight percent, and beeswax in a preferred amount between about 2 and 10 weight percent. In addition, slippery elm bark may be added to the formulation in an amount between about 0.25 and 1.50 weight percent. Further, benzoin styrax may be added to the inventive formulation in an amount between about 2.0 and 17.5 weight percent.

As a further additive to the inventive formulation, one or more essential oils may be included within the inventive formulation. Such oils are preferably selected from wintergreen essential oil, lavender essential oil and bergamot essential oils. The oils are added in an amount between about 1.25 and 7.50 weight percent.

The inventive formulation is used by application to the skin in order to treat various skin afflictions including chafes, burns, eczema, abrasions, sores, blisters, irritations, bites and stings, psoriasis, etc. Application of the inventive formulation helps to soften, soothe, protect and heal these and other types of skin afflictions.

Accordingly, it is an object of the invention to provide an improved cosmetic skin formulation.

Another object of the invention is to provide a formulation for treating various afflictions of the skin.

Other objects and advantages will be obvious from the following description.

DETAILED DESCRIPTION OF THE INVENTION

The first required ingredient of the inventive formulation is leaf lard as a base. Leaf lard, also known as a axungia, is high in oleic and linoleic acids and is used as an emollient. The leaf lard base preferably comprises between about 55 and 80 weight percent of the inventive formulation.

The next required ingredient in the inventive formulation is zinc oxide, which is present in an amount between about 10 and 25 weight percent. Zinc oxide promotes healing.

The next required ingredient is beeswax, which is present in the inventive formulation in an amount between about 2 and 10 weight percent. Beeswax, which contains Vitamin A, helps retain natural skin moisture and relieves itching.

Optionally, slippery elm bark may be added to the formulation in an amount between about 0.25 and 1.5 weight percent. Slippery elm bark helps relieve itching, irritation and inflammation.

In addition, benzoin styrax may be also added to the formulation in an amount between about 2.0 and 17.5 weight percent. Benzoin styrax, a natural preservative, helps soothe and stimulates healing.

One or more essential oils may be added to the formulation in an amount between about 1.25 and 7.50 weight percent. Such oils include wintergreen, lavender and bergamot. These oils promote cell rejuvenation and provide aromatic properties. If added, wintergreen oil should be present in an amount between about 0.75 and 3.25 weight percent. If added, lavender oil should be present in an amount between about 0.40 and 3.25 weight percent. If added, bergamot oil should be present in an amount between about 0.40 and 3.25 weight percent.

One embodiment of the inventive formulation is as follows:

1 lb. leaf lard
2 oz beeswax (range from ½ oz to 2 oz)
3.89 grams slippery elm bark (powder)
4 oz zinc oxide (range from 2 ½-6 oz)
1 oz benzoin styrax (powder)
10-20 ml wintergreen essential oil
7-15 ml lavender essential oil
2-10 ml bergamot essential oil In preparing the inventive formulation, axungia, or leaf fat, which surrounds the kidneys of a hog, is used. This fat must be rendered within one week of slaughter or else frozen. Once the leaf fat is rendered, it is called leaf lard, which is the highest grade of lard that is known.

In order to render the leaf fat into leaf lard, the leaf fat is first cut into 1 inch squares and then heated, preferably, by placing the squares in a stainless steel pot with enough water to cover the bottom; the temperature of heating should not exceed 180° F. (alternatively, the leaf fat squares may be placed into an oven via a pan; the temperature should not exceed 250° F.). After an hour, the melted fat in the pot or pan should be stirred, and stirring should continue on a regular basis. The fat squares should also be turned every 15 minutes to ½ hour in order for rendering to occur properly. This rendering process should be carried out from 3 ½-5 hours, during which stirring should take place on a regular basis.

Once rendering is completed, any remaining fat pieces are removed and the liquid is strained through a metal mesh strainer. The liquid comprises the leaf lard.

Next, powdered benzoin styrax is added to the liquid leaf lard in order to macerate in the lard for up to 2 hours. This mixture is then strained a second time through a fine mesh strainer. Melted beeswax is now added into the mixture. Then the slippery elm bark, followed by the zinc oxide, is added. The entire mixture is allowed to meld together (on a low heat setting of approx. 80-120° F.). The mixture is removed from the heat and the various essential oils are then added while the mixture is constantly stirred. The mixture is then poured into tins, cooled and then packaged.

Significantly, during manufacture, it is important not to whip or churn the mixture.

The scope of the invention will now be set forth in the following claims.

The invention claimed is:

1. A topical cosmetic skin formulation comprising:
   leaf lard as a base, wherein the leaf lard is rendered at a temperature not exceeding 180° F.;
   zinc oxide in an amount between about 10 and 25 weight percent; and beeswax in an amount between about 2 and 10 weight percent;

wherein a mixture of the leaf lard, zinc oxide and beeswax is melded together at a temperature of approximately 80° F. to approximately 120° F.

2. The formulation of claim 1, wherein the leaf lard is present in an amount between about 55 and 80 weight percent.

3. The formulation of claim 1, further including slippery elm bark in an amount between about 0.25 and 1.50 weight percent.

4. The formulation of claim 1, further including Styrax benzoin resin in an amount between about 2.0 and 17.5 weight percent.

5. The formulation of claim 1, further including one or more essential oils selected from the group consisting of wintergreen oil, lavender oil and bergamot oil.

6. The formulation of claim 5, wherein said essential oils are present in an amount between about 1.25 and 7.50 weight percent.

7. The formulation of claim 5, wherein the essential oil is wintergreen oil in an amount between about 0.75 and 3.25 weight percent.

8. The formulation of claim 5, wherein the essential oil is lavender oil in an amount between about 0.40 and 3.25 weight percent.

9. The formulation of claim 5, wherein the essential oil is bergamot oil in an amount between about 0.40 and 3.25 weight percent.

10. The formulation of claim 1, further including slippery elm bark in an amount between about 0.25 and 1.50 weight percent and Styrax benzoin resin in an amount between about 2.0 and 17.5 weight percent.

* * * * *